United States Patent

Pfirmann et al.

[11] Patent Number: 5,874,608
[45] Date of Patent: Feb. 23, 1999

[54] PROCESS FOR THE PREPARATION OF ESTERS OF AROMATIC CARBOXYLIC ACID

[75] Inventors: Ralf Pfirmann, Griesheim; Theodor Papenfuhs, Frankfurt, both of Germany

[73] Assignee: Hoechst Aktiengesellschaft, Frankfurt, Germany

[21] Appl. No.: 858,357

[22] Filed: May 19, 1997

[30] Foreign Application Priority Data

May 20, 1996 [DE] Germany .................. 196 20 191.8

[51] Int. Cl.$^6$ .................................................. C07C 69/76
[52] U.S. Cl. ......................... 560/8; 560/9; 560/18; 560/19; 560/45; 560/46; 560/47; 560/55; 560/64; 560/65; 560/67; 560/76; 560/83; 560/96; 560/100; 560/102; 560/103
[58] Field of Search .................. 560/8, 9, 18, 19, 560/45, 46, 47, 55, 64, 65, 67, 76, 83, 96, 100, 102, 103

[56] References Cited

U.S. PATENT DOCUMENTS 5,424,479 6/1995 Müller et al. ........................... 560/64

FOREIGN PATENT DOCUMENTS

| 2182350 | 2/1997 | Canada . |
| 640582 | 3/1995 | European Pat. Off. . |
| 757028 | 2/1997 | European Pat. Off. . |

OTHER PUBLICATIONS

J. Barry et al, "Solid–Liquid Phase–Transfer Catalysis without added solvent. A Simple, Efficient, and Inexpensive Synthesis of Aromatic Carboylic Ester by Alkylation of Potassium Carboxylates" *Synthesis* 1 Jan. 1985, pp. 40–45.

*Primary Examiner*—Rosalynd Keys
*Attorney, Agent, or Firm*—Connolly and Hutz

[57] ABSTRACT

The present invention relates to a process for the preparation of compounds of the formula (1)

$$R^1R^2R^3R^4R^5\text{ArCOOR} \tag{1}$$

in which $R^1$, $R^2$, $R^3$, $R^4$ and $R^5$ are identical or different and are hydrogen, a halogen, an alkyl or alkoxy group having 1 to 6 carbon atoms or OR, NHR, NR$_2$, SR or COOR, in which R is an alkyl radical having 1 to 4 carbon atoms, Ar is an aryl radical having 6 to 12 carbon atoms and the radical R shown in formula (1) has the above meaning, by reacting a compound of the formula (2)

$$R^1R^2R^3R^4R^5\text{ArCOOH} \tag{2}$$

in which $R^1$, $R^2$, $R^3$, $R^4$ and $R^5$ are identical or different and are hydrogen, a halogen, an alkyl or alkoxy group having 1 to 6 carbon atoms, OH, NH$_2$, NHR, SH or COOH and Ar has the same meaning as in formula (1), with a sulfate of the formula (RO)$_2$SO$_2$, in which R has the above meaning, in the presence of a water-insoluble tertiary amine and water at a temperature of 10° to 120° C. in the presence or absence of a water-insoluble solvent and with the addition of a base, at a pH of 5 to 12.

31 Claims, No Drawings

PROCESS FOR THE PREPARATION OF ESTERS OF AROMATIC CARBOXYLIC ACID

The present invention relates to a process for the preparation of esters of aromatic carboxylic acids by alkylation of aromatic carboxylic acids which possibly contain further alkylatable substituents.

Esters of aromatic carboxylic acids have acquired great industrial importance because of their diverse properties. They can be used in various sectors. Salicylic acid esters are used as odoriferous substances. Phthalic acid esters of higher alcohols are employed as plasticizers for polyvinyl chloride (PVC), and phthalic acid esters of polyhydric alcohols are used for raw materials for paints. Some esters of p-aminobenzoic acid, for example ethyl p-aminobenzoate (Anaesthesin) or β-diethylamino p-aminobenzoate (Procaine) have become established as local anesthetics in the form of their hydrochlorides (Beyer-Walter, Lehrbuch der organischen Chemie [Textbook of organic chemistry], 21st edition, pages 553, 559 and 551; S. Hirzel Verlag Stuttgart 1988). Esters of fluorinated benzoic acids, for example esters of 2,3,4,5-tetrafluorobenzoic acid (Drugs of the future 1993, Volume 18 Issue 8, pages 717 to 720) or the methyl ester of 3-methoxy-2,4,5-trifluorobenzoic acid (U.S. Pat. No. 5,047,538), can be used as precursors for the preparation of antibacterial agents from the fluoroquinolinecarboxylic acid series or can be converted into further precursors required for the preparation of these antibacterial agents.

Carboxylic acid esters can chiefly be prepared by two routes:

1. By esterification of the carboxylic acids with an excess of alcohol under acid conditions, water being split off.
2. By alkylation of a carboxylic acid salt by means of an alkylating agent, for example an alkyl halide. In this process, the carboxylic acid salt is usually used in the form of an aqueous solution prepared by reaction of the carboxylic acid with an aqueous base, or is prepared in situ by reaction of the carboxylic acid with a base dissolved in water.

In Synthesis (1985), 40–45, J. Barry describes a preparation of aromatic carboxylic acid esters by alkylation of potassium salts of aromatic carboxylic acids without addition of a solvent, but using a phase transfer catalyst. In addition to alkyl halides, dimethyl sulfate and diethyl sulfate are employed as alkylating agents.

The potassium carboxylate is prepared either by dissolving the carboxylic acid in the stoichiometric amount of an aqueous potassium hydroxide solution, subsequently evaporating off the water and grinding the dry potassium carboxylate to give a fine powder (method A), or by mixing the finely divided carboxylic acid, finely divided potassium hydroxide and the ammonium salt employed as the phase transfer catalyst, and by subsequent heating of this mixture to 140° C. and final grinding of the melt cake (method B).

The phase transfer catalyst and then the alkylating agent, for example dimethyl sulfate, are added to the potassium carboxylate prepared according to method A, while the alkylating agent is added directly to the potassium carboxylate prepared according to method B, which already contains the phase transfer catalyst.

The mixture is shaken, reacted under the reaction conditions stated and then diluted twice with ether, filtered over a short column packed with an auxiliary and then purified by chromatography or crystallization.

Aromatic carboxylic acids which optionally contain further alkylatable substituents can be reacted by this method using, for example, dimethyl sulfate.

The process described above has several disadvantages. On the one hand, both the potassium carboxylate prepared according to method A and that prepared according to method B require a considerable expenditure of work, for example evaporation of water and mechanical grinding of the carboxylic acid, the potassium hydroxide and the potassium carboxylate cake. On the other hand, working up of the reaction mixture obtained (dilution twice with ether, filtration and subsequent purification by column chromatography or crystallization) also proves to be quite cumbersome.

The ammonium salts used as the phase transfer catalyst, moreover, enter the waste water, pollute it and lead to problems in working up of the waste water, since they are difficult to break down.

It was therefore a worthwhile object to provide a process for the preparation of aromatic carboxylic acids which does not have the disadvantages described above and which furthermore also allows alkylation of further alkylatable substituents, in addition to alkylation of the carboxyl group.

This object is achieved by a process for the preparation of compounds of the formula (1)

$$R^1R^2R^3R^4R^5ArCOOR \quad (1)$$

in which $R^1$, $R^2$, $R^3$, $R^4$ and $R^5$ are identical or different and are hydrogen, a halogen, an alkyl or alkoxy group having 1 to 6 carbon atoms or OR, NHR, $NR_2$, SR or COOR, in which R is an alkyl radical having 1 to 4 carbon atoms, Ar is an aryl radical having 6 to 12 carbon atoms and the radical R shown in formula (1) has the above meaning. It comprises reacting a compound of the formula (2)

$$R^1R^2R^3R^4R^5ArCOOH \quad (2)$$

in which $R^1$, $R^2$, $R^3$, $R^4$ and $R^5$ are identical or different and are hydrogen, a halogen, an alkyl or alkoxy group having 1 to 6 carbon atoms, OH, $NH_2$, NHR, SH or COOH and Ar has the same meaning as in formula (1), with a sulfate of the formula $(RO)_2SO_2$, in which R has the above meaning, in the presence of a water-insoluble tertiary amine and water at a temperature of 10° to 120° C. in the presence or absence of a water-insoluble solvent and with the addition of a base, at a pH of 5 to 12.

The process according to the invention has several advantages.

On the one hand, it is not necessary to employ the aromatic carboxylic acid to be reacted in the form of its anhydrous potassium salts, but it is sufficient to prepare an aqueous solution of a salt of the aromatic carboxylic acid in situ from the aromatic carboxylic acid. On the other hand, in a large number of cases it is not necessary to employ a phase transfer catalyst which is difficult to break down. As a result, pollution of the waste water and trouble during working up of the waste water are also avoided.

Another advantage is that when the reaction has ended, only the organic phase, which comprises the water-insoluble tertiary amine and the valuable product, must be separated from the aqueous phase. Further working up is, as a rule, carried out by distillation. As a result, the use of a problematic solvent, for example ether, is avoided.

It is moreover to be regarded as surprising that the water-insoluble tertiary amine does not react at all or reacts to only a quite small extent with the dialkyl sulfate. As a result of this, the process according to the invention does not lead to an increased consumption of dialkyl sulfate.

It is also of advantage that after the valuable product, i.e. the compounds of the formula (1), has been separated off, the water-insoluble tertiary amine which remains can be employed again in the reaction. As a result, the demand for auxiliaries, which can lead to an additional pollution of the waste water, is also kept low.

The process according to the invention enables not only the carboxyl group in the compound of the formula (2) but also further alkylatable groups present in the aromatic carboxylic acid of the formula (2), namely the OH, $NH_2$, NHR, SH and COOH group, to be alkylated. If desired, the alkylation of these groups of different reactivity can also be carried out at a single pH. The process according to the invention is consequently quite simple.

However, the reaction can also be allowed to proceed at different pH values, in order first to work at a higher pH and thereafter to work at a lower pH. This variant of the process is also quite simple to carry out, since the reaction does not have to be interrupted for this purpose, but can be carried out in the same reaction medium.

A compound (2) in which $R^1$ and $R^2$ are identical or different and are hydrogen, an alkyl group having 1 to 6 carbon atoms, OH, $NH_2$ or COOH, in particular hydrogen, OH or COOH, is usually employed.

A compound of the formula (2) in which $R^1$ or $R^2$ is OH or COOH, in particular OH, can also be employed. The other four radicals $R^1$, $R^3$, $R^4$, $R^5$ or $R^2$, $R^3$, $R^4$, $R^5$ are in this case identical or different and are hydrogen, a halogen or an alkyl or alkoxy group having 1 to 6 carbon atoms, in particular hydrogen, fluorine, chlorine or an alkyl group having 1 to 6 carbon atoms, preferably hydrogen or fluorine.

In a number of cases, a compound of the formula (2) in which $R^3$, $R^4$ and $R^5$ are identical or different and are hydrogen, a halogen or an alkyl or an alkoxy group having 1 to 6 carbon atoms, in particular hydrogen, fluorine, chlorine or an alkyl group having 1 to 6 carbon atoms, preferably hydrogen or fluorine, can be employed in the reaction.

A compound of the formula (2) in which Ar, as already mentioned above, is an aryl radical having 6 to 12 carbon atoms, in particular a phenyl radical, biphenyl radical or naphthyl radical, preferably a phenyl radical, is employed in the reaction.

Examples which may be mentioned of compounds of the formula (2), without claim to completeness, are 2-chlorobenzoic acid,
3-chlorobenzoic acid
4-chlorobenzoic acid,
2-fluorobenzoic acid,
3-fluorobenzoic acid,
4-fluorobenzoic acid,
2-bromobenzoic acid,
3-bromobenzoic acid,
4-bromobenzoic acid,
2,4-dichlorobenzoic acid,
2,4-difluorobenzoic acid,
3,4-difluorobenzoic acid,
3,4-dichlorobenzoic acid,
2,5-dichlorobenzoic acid,
2,6-difluorobenzoic acid,
2,3,6-trifluorobenzoic acid,
2,4,5-trifluorobenzoic acid,
2,4,5-trichlorobenzoic acid,
2,3,4,5-tetrachlorobenzoic acid,
2,3,4,5-tetrafluorobenzoic acid,
2,3,5,6-tetrafluorobenzoic acid,
pentafluorobenzoic acid,
pentachlorobenzoic acid,
2-chloro-3,4,5-trifluorobenzoic acid,
2,3-dichloro-4,5-difluorobenzoic acid,
2,4,5-trifluoro-3-chlorobenzoic acid,
2,4-difluoro-3,5-dichlorobenzoic acid,
2,6-difluoro-3,5-dichlorobenzoic acid,
2-hydroxybenzoic acid,
3-hydroxybenzoic acid,
4-hydroxybenzoic acid,
2-chloro-4-hydroxybenzoic acid,
2-fluoro-4-hydroxybenzoic acid,
2,3, 5-trifluoro-4-hydroxybenzoic acid,
2,4, 5-trifluoro-3-hyd roxybenzoic acid,
4-hydroxy-2,3,5,6-tetrafluorobenzoic acid,
5-chloro-2-hydroxybenzoic acid,
5-fluoro-2-hydroxybenzoic acid,
4-chloro-2-hydroxybenzoic acid,
5-chloro-2-hydroxybenzoic acid,
4-chloro-2-aminobenzoic acid,
4-fluoro-2-aminobenzoic acid,
5-fluoro-2-aminobenzoic acid,
5-chloro-2-aminobenzoic acid,
3-amino-2,4,5-trifluorobenzoic acid,
4-aminobenzoic acid,
4-amino-2-chlorobenzoic acid,
4-amino-2-fluorobenzoic acid,
4-amino-2,3,5-trifluorobenzoic acid,
6-methyl-3-amino-2,4, 5-trifluorobenzoic acid,
3-hydroxy-2,4-difluorobenzoic acid,
4-hydroxy-3-fluorobenzoic acid,
4-hydroxy-3-chlorobenzoic acid,
4-hydroxy-3,5-dichlorobenzoic acid,
4-hyd roxy-3,5-difluorobenzoic acid,
3-hydroxytetrafluorobenzoic acid,
2-hydroxytetrafluorobenzoic acid,
3-methyl-2,4,5-trifluorobenzoic acid,
3-ethyl-2,4,5-trifluorobenzoic acid and
6-methyl-3-hydroxy-2,4,5-trifluorobenzoic acid,
in particular 2,3,6-trifluorobenzoic acid, 2,4,5-trifluorobenzoic acid,
2,4,5-trichlorobenzoic acid, 2,3,4,5-tetrachlorobenzoic acid,
2,3,4,5-tetrafluorobenzoic acid, 2,3,5,6-tetrafluorobenzoic acid,
2-hydroxybenzoic acid, 3-hydroxybenzoic acid, 4-hydroxybenzoic acid,
2-chloro-4-hydroxybenzoic acid, 2-fluoro-4-hydroxybenzoic acid,
2,3,5-trifluoro-4-hydroxybenzoic acid, 2,4,5-triluoro-3-hydroxybenzoic acid,
4-hydroxy-2,3,5,6-tetrafluorobenzoic acid, 5-chloro-2-hydroxybenzoic acid,
5-fluoro-2-hydroxybenzoic acid, 4-chloro-2-hydroxybenzoic acid, 5-chloro-2-hydroxybenzoic acid, 3-hydroxy-2,4-difluorobenzoic acid, 4-hydroxy-3-fluorobenzoic acid, 4-hydroxy-3-chlorobenzoic acid, 4-hydroxy-3,5-dichlorobenzoic acid, 4-hydroxy-3,5-difluorobenzoic acid, 3-hydroxytetrafluorobenzoic acid, 2-hydroxytetrafluorobenzoic acid and 6-methyl-3-hydroxy-2,4,5-trifluorobenzoic acid.

The compound of the formula (2) is reacted with a sulfate of the formula $(RO)_2SO_2$, in which R is an alkyl radical having 1 to 4 carbon atoms. Dimethyl sulfate, diethyl sulfate or dibutyl sulfate, preferably dimethyl sulfate or diethyl sulfate, is employed in particular as the sulfate of the formula $(RO)_2SO_2$.

The reaction is allowed to proceed in the presence of a water-insoluble tertiary amine. The term water-insoluble tertiary amine is understood as meaning those amines which either dissolve to only a small extent or do not dissolve at all in water.

A trialkylamine having 4 to 20 carbon atoms per alkyl radical, a mixture of these trialkylamines, an N-containing heterocyclic compound or a mixture of the above amines, in particular a trialkylamine having 6 to 14 carbon atoms per alkyl radical, a mixture of these trialkylamines, an optionally alkylated pyridine or quinoline, for example collidine, lutidine or a picoline, or a mixture of these tertiary amines is usually employed as the water-insoluble tertiary amine. The abovementioned trialkylamines contain straight-chain and/ or branched alkyl radicals. The alkyl radicals can be identical or different. Mixtures of the abovementioned trialkylamines are particularly suitable.

In a number of cases, a mixture of trialkylamines having 6 to 12 carbon atoms per alkyl radical, which contain identical or different straight-chain or branched alkyl radicals, has proven particularly suitable.

Since the reaction is carried out in the presence of the water-insoluble tertiary amine and water, the reaction proceeds in a reaction medium comprising two liquid phases. Good thorough mixing of the two phases must be ensured in order to promote the reaction. When the reaction has ended, these two phases usually demix, so that separation of the aqueous phase from the organic phase presents no problems.

The following compounds may be mentioned as water-insoluble trialkylamines of the abovementioned type, without claim to completeness: tri-n-butylamine, triisobutylamine, tri-n-pentylamine, triisopentylamine, tri-n-hexylamine, tri-isohexylamine, tri-n-heptylamine, triisoheptylamine, tri-n-octylamine, triisoctylamine, tri-n-decylamine, triisodecylamine, tri-n-dodecylamine, triisododecylamine, trialkylamines with straight and/or branched chains having 6 to 14 carbon atoms, pyridine, α-picoline, β-picoline, y-picoline, 2,4-dimethylpyridine(α, γ-lutidine), 2,6-di-tert-butylpyridine, 2,4,6-trimethylpyridine (collidine), triethylpyridine, quinoline, methylquinolines, ethylquinolines, mixed amines, such as butyidihexylamine, dioctyadecylamines hexyldioctylamine, dihexyloctylamine, diheptyloctylamine, didecyloctylamine, didodecyloctylamine, didodecyldecylamine, didecyldodecylamine, dioctyldodecylamine, dinonyloctylamine, dinonyvdecylamine and dinonyldodecylamine, and mixtures thereof.

In a large number of cases it has proven sufficient to carry out the reaction at 20° to 80° C., in particular at 30° to 60° C.

The reaction is carried out in the presence or absence of a water-insoluble solvent. An aliphatic hydrocarbon, a halogenated aliphatic hydrocarbon, an aromatic hydrocarbon, a halogenated aromatic hydrocarbon, an aromatic ether or a mixture of these solvents can be employed as the water-insoluble solvent. Water-insoluble solvents which may be mentioned at this point, without making claims to completeness, are hexane, heptane, octane, dichloromethane, trichloromethane, toluene, o-xylene, m-xylene, p-xylene, mixtures of isomeric xylenes, ethylbenzene, butylbenzene, chlorobenzene, o-dichlorobenzene, m-dichlorobenzene, p-dichlorobenzene, chlorotoluene, m-chlorotoluene, p-chlorotoluene, biphenyl, diphenylmethane or diphenyl ether. Mixtures of these solvents can also be used.

The reaction can be carried out in the absence or presence of a phase transfer catalyst.

In individual cases it may be helpful, for example for the purpose of improving thorough mixing, minimizing the amount and consumption of dialkyl sulfate and/or increasing the rate of reaction, to carry out the reaction in the presence of a phase transfer catalyst. A quaternary ammonium or phosphonium salt or mixtures thereof, in particular a quaternary ammonium salt of the formula

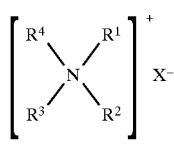

in which $R^1$, $R^2$, $R^3$ and $R^4$ are identical or different and are hydrocarbon radicals having a total of 10 to 50 carbon atoms and X is a halide ion, hydrogen sulfate ion or hydroxyl ion, in particular a chloride, bromide or hydrogen sulfate ion, or a mixture of such quaternary ammonium salts, is usually used as the phase transfer catalyst.

Tetra($C_1$–$C_{20}$)alkylammonium salts, tri($C_1$–$C_{20}$) alkylbenzylammonium salts and di($C_1$–$C_{20}$) alkyldibenzylammonium salts, the benzyl radical of which is unsubstituted or substituted by Cl, Br, ($C_1$–$C_4$)alkyl or ($C_1$–$C_4$)alkoxy, and in particular is unsubstituted, are suitable as the phase transfer catalyst.

Phase transfer catalysts which can be employed are those which are described, for example in DE-A 2 634 419, DE-A 3 120 912 and DE-A 3 737 919, for example tetrabutylammonium bromide, tetramethylammonium chloride, tetramethylammonium hydrogen sulfate, benzyldodecyidimethylammonium chloride, stearyidimethylbenzylammonium halide, hexadecyltrimethylammonium halide or a quaternary ammonium halide containing one or more, in particular one or two, coconut($C_{10}$–$C_{18}$)alkyl radicals, for example dicoconut($C_{10}$–$C_{18}$)alkyldimethylammonium halide or dimethylbenzylcoconut($C_{10}$–$C_{18}$)alkylammonium halide, in which the halide is, in particular, chloride or bromide. Dimethylbenzylcoconut($C_{10}$–$C_{18}$)alkylammonium chloride having an average molecular weight of 382.5 has proven particularly suitable, and is preferably used as a 50% strength aqueous solution (Dodigen 226).

The phase transfer catalyst is usually employed in an amount of 0.05 to 10, in particular 0.2 to 2.5, preferably 0.25 to 1.5% by weight, based on the aqueous phase.

An aqueous solution and/or a suspension of an alkali metal hydroxide or alkaline earth metal hydroxide, in particular an aqueous LiOH, NaOH or KOH solution, preferably an aqueous NaOH or KOH solution, or a mixture of these aqueous solutions, is employed as the base. The aqueous solution and/or suspension usually comprises 5 to 50, in particular 10 to 40, preferably 20 to 35% by weight of alkali metal hydroxide or alkaline earth metal hydroxide.

For a number of cases, it has proven beneficial to carry out the reaction at a pH of 6 to 10, in particular at a pH of 7 to 8.5.

The process can be carried out without great industrial expenditure while observing the abovementioned reaction conditions.

Water, the aromatic carboxylic acid (compound of the formula (2)), the water-insoluble tertiary amine and, if appropriate, the water-insoluble solvent are initially introduced into the reaction vessel in any desired sequence and the desired pH is then established by addition of a base, while stirring. It is also possible to employ an aqueous solution of the aromatic carboxylic acid or an aqueous solution of a salt of the aromatic carboxylic acid. It is also possible to employ in the reaction a mixture which originates, for example, from a previous reaction step, comprising water, the aromatic carboxylic acid, the water-insoluble tertiary amine and, if appropriate, the water-insoluble solvent. In this case, the desired pH is likewise established by addition of a base, while stirring.

The sulfate of the formula $(RO)_2SO_2$ and the base are then added to an extent such that the given pH is maintained.

The water-insoluble tertiary amine permits use in a wide range of amounts. The water-insoluble tertiary amine and the aromatic carboxylic acid (compound of the formula (2)) are usually employed in a molar ratio of (0.01 to 10):1, in particular (0.05 to 3):1, preferably (0.05 to 1):1, particularly preferably (0.1 to 0.5):1. The content of water can be chosen within wide limits. The ratio of the volume of the aqueous phase to the volume of the organic phase is usually (0.05 to 50):1, in particular (0.05 to 20):1, preferably (0.1 to 10):1.

In this connection, it may be pointed out that the organic phase comprises not only the water-insoluble tertiary amine but also the valuable product, in particular the compound of the formula (1), and, where appropriate, the water-insoluble solvent.

The water-insoluble solvent and the aromatic carboxylic acid (compound of the formula (2)) are employed in a weight ratio of (0.05 to 100):1, in particular (0.3 to 10):1, preferably (0.8 to 5):1.

The sulfate of the formula $(RO)_2SO_2$ is employed in a ratio, based on each group R to be introduced into the compound of the formula (2), of (1 to 10):1, in particular (1.1 to 5):1, preferably (1.2 to 1.5):1. If the starting material also comprises further substances which react with the sulfate, in addition to the compound of the formula (2), the amount of sulfate is to be increased accordingly.

It goes without saying that the appropriate safety measures are to be observed when handling the sulfate, in particular when handling dialkyl sulfates, more precisely dimethyl sulfate. 1 to 1.5, in particular 1.01 to 1.2, preferably 1.01 to 1.1 equivalents of base are employed per mole of sulfate of the formula $(RO)_2SO_2$ reacted with the compound of the formula (2).

When the reaction has ended, it is ensured that sulfate still present is destroyed, for example by addition of aqueous alkali, aqueous ammonia or an aqueous ammonium salt solution.

The organic phase, which comprises the valuable product, is then separated from the aqueous phase and the organic phase is worked up, for example by distillation.

If desired, however, when the reaction has ended, the water-insoluble solvent can also be added, for example in order to facilitate the phase separation. The process can be carried out continuously or discontinuously. It allows working both under reduced pressure and under atmospheric pressure or increased pressure.

The following examples describe the present invention, without limiting it thereto.

Experimental part

EXAMPLE 1

Preparation of methyl 4-hydroxybenzoate and methyl 4-methoxybenzoate

The reaction proceeds in accordance with the following equation:

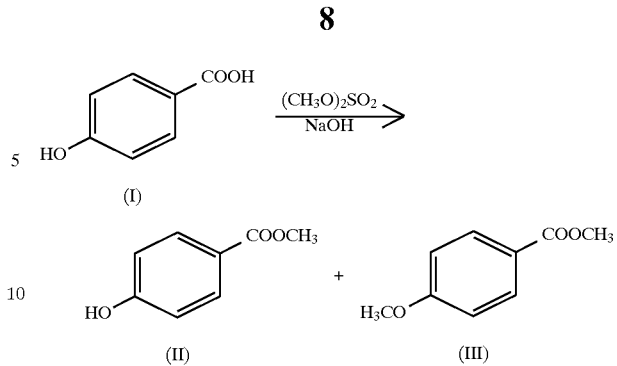

34.5 g (0.25 mol) of 4-hydroxybenzoic acid (I) and 150 g of water are initially introduced into and mixed in a glass flask. The 4-hydroxybenzoic acid is partly dissolved, a milky-cloudy suspension forming. 5 g of a mixture of trialkylamines having 8 to 10 carbon atoms per alkyl radical (Hostarex A327, a commercial product from HOECHST AG) are dissolved in 30 g of xylene, this solution is added to the suspension and the mixture is heated to 45° C. The pH is checked by means of a calibrated pH electrode immersed in the aqueous phase. The pH is brought to 8 by dropwise addition of a 10% strength by weight aqueous NaOH solution. 88.2 g (0.7 mol) of dimethyl sulfate are then added dropwise in the course of 3 hours, with intensive stirring. The pH is kept in a range from 7.5 to 8.5 by dropwise addition of aqueous NaOH (10% by weight). When the addition of dimethyl sulfate has ended, the mixture is stirred overnight. Two phases form; an upper, organic phase, which comprises the valuable product (mixture of methyl 4-hydroxybenzoate(II) and methyl 4-methoxybenzoate(III)), and a lower, aqueous phase.

The organic phase is separated off. According to HPLC analysis, in addition to 15% of solvents (xylene and tertiary amines), it comprises 40% (corresponding to 14.7 g=0.089 mol; 35.4% of theory) of methyl 4-methoxybenzoate and 44% (corresponding to 16.2 g=0.106 mol; 42.4% of theory) of methyl 4-hydroxybenzoate. In the aqueous phase—determined as HPLC area-%, calculated without water and without salt contents—51% of starting material (4-hydroxybenzoic acid), 37% of methyl 4-hydroxybenzoate and 11.6% of methyl 4-methoxybenzoate are present. By-products are found only to a quite small extent (<1%). The selectivity of the formation of (methyl 4-hydroxybenzoate+methyl 4-methoxybenzoate) is ≧ 95%.

If the reaction is carried out at 35° to 40° C., while keeping the pH constant at 7 to 7.5 and using the above-mentioned starting substances and amounts, 77.2 g of organic phase are obtained. This organic phase comprises (determined by means of HPLC analysis) 39.4 g (0.239 mol=95.4% of theory) of methyl 4-methoxybenzoate and 0.8 g (0.005 mol=2.1% of theory) of methyl 4-hydroxybenzoate. The aqueous phase comprises only traces of 4-methoxybenzoic acid.

EXAMPLE 2

Preparation of methyl 3-methoxy-2,4,5-trifluorobenzoate a) Preparation of 3-hydroxy-2,4,5-trifluorobenzoic acid by decarboxylation of 4-hydroxy-3,5,6-trifluorophthalic acid The reaction proceeds in accordance with the following equation:

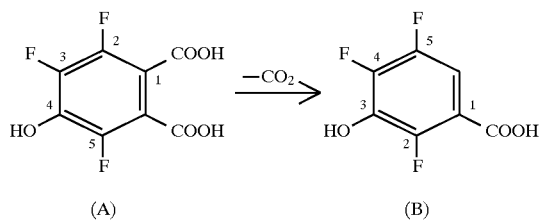

(A)                (B)

255 g of an aqueous solution which comprises 20.6 g (87.3 mmol) of 4-hydroxy-3,5,6-trifluorophthalic acid (A) are initially introduced into a glass flask, while stirring, and 20 g of a mixture of trialkyl-amines having 8 to 10 carbon atoms per alkyl radical (Hostarex A327; a commercial product of HOECHST AG) are added. 49 g of a 30% strength by weight aqueous hydrochloric acid are added, with thorough mixing. The pH is checked by means of a calibrated pH electrode immersed in the aqueous phase. After addition of the hydrochloric acid, the pH is 5. The mixture is then heated to 105°, with thorough mixing, the pH is kept constant at pH=6 by addition of a total of 13.5 g of a 30% strength by weight aqueous hydrochloric acid and the mixture is allowed to react for 7 hours. As a result of the decarboxylation which proceeds here, the 4-hydroxy-3,5,6-trifluorophthalic acid (A) is converted into 3-hydroxy-2,4,5-trifluorobenzoic acid (B).

b) Preparation of methyl 3-methoxy-2,4,5-trifluorobenzoate

The reaction proceeds in accordance with the following equation

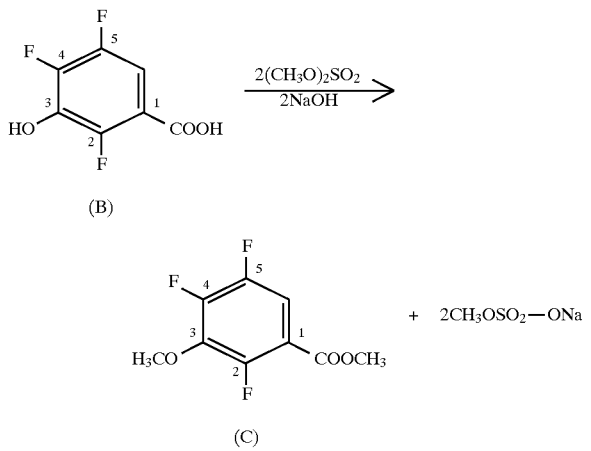

34 g of a 10% strength by weight aqueous sodium hydroxide solution are added to the reaction mixture obtained from Example 2a), which comprises 3-hydroxy-2,4,5-trifluorobenzoic acid (B), while stirring. The pH of the reaction mixture comprising the water, the mixture of water-insoluble trialkylamines having 8 to 10 carbon atoms per alkyl radical (Hostarex A 327) and the aromatic carboxylic acid, that is to say the 3-hydroxy-2,4,5-trifluorobenzoic acid, is checked by means of a calibrated pH electrode immersed in the aqueous phase. After addition of the sodium hydroxide solution, the pH is 7. A total of 90 g (0.72 mol) of dimethyl sulfate are then added dropwise at a temperature of 40° C. over a period of 80 minutes and the pH is kept constant at 7 by addition of a total of 37 g of a 10% strength by weight aqueous sodium hydroxide solution. 20 g of diphenylmethane are then added and the organic phase (50 g) is separated off from the aqueous phase.

The organic phase comprises, determined by calibrated (HPLC) liquid chromatography analysis, 17.6 g (80 mmol) of methyl 3-methoxy-2,4,5-trifluorobenzoate, corresponding to a yield of 91.6% over 2 stages, based on the 4-hydroxy-3,5,6-trifluorophthalic acid employed.

c) If Example 2b) is repeated, but the abovementioned amount of diphenylmethane is added as early as during the methylation, 17.4 g (79 mmol) of methyl 3-methoxy-2,4,5-trifluorobenzoate are obtained, corresponding to a yield of 90.5% based on the 4-hydroxy-3,5,6-trifluorophthalic acid employed.

Comparison example

Preparation of methyl 3-methoxy-2,4,5-trifluorobenzoate without addition of a water-insoluble tertiary amine The reaction proceeds in accordance with the following equation:

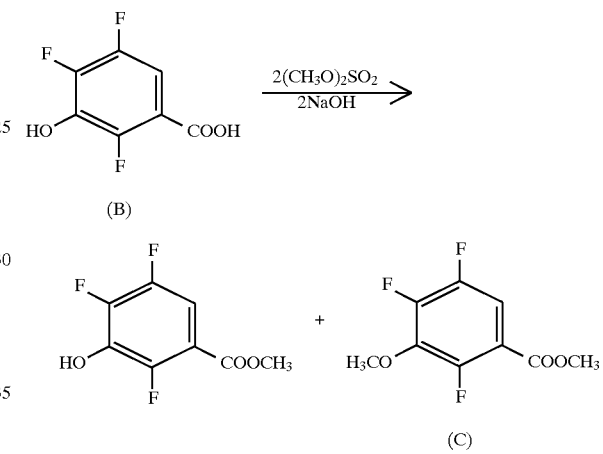

299 g of an aqueous solution which comprises 15.6 g (81 mmol) of 3-hydroxy-2,4,5-trifluorobenzoic acid (B) are initially introduced into a glass flask and, instead of the water-insoluble trialkylamine or amine mixture, 10 g of xylene are added. A 30% strength by weight aqueous hydrochloric acid is added up to a pH of 7, and the pH is checked by means of a calibrated pH electrode immersed in the aqueous phase. A total of 156.8 g (1.41 mol) of dimethyl sulfate are then added dropwise at a temperature of 40° C. over a period of 3.5 hours and the pH is kept constant at 7 by addition of a total of 46.6 g of a 10% strength by weight aqueous sodium hydroxide solution. In spite of a considerable excess of dimethyl sulfate, the dimethylated product, that is to say methyl 3-methoxy-2,4,5-trifluorobenzoate, has formed in only small amounts. 3-Hydroxy-2,4,5-trifluorobenzoic acid (B) corresponding to a yield of 8.6%, methyl 3-hydroxy-2,4,5-trifluorobenzoate corresponding to a yield of 67% and methyl 3-methoxy-2,4,5-trifluorobenzoate (C) corresponding to a yield of only 8.7%, in each case based on the 3-hydroxy-2,4,5-trifluorobenzoic acid employed, are found.

The problem of scant formation of methyl 3-methoxy-2,4,5-benzoate can be solved by addition of a small amount (2 g) of the mixture of different water-insoluble trialkylamines used in Example 2b).

2 g of the mixture of trialkylamines mentioned in Example 2b) are added to the reaction mixture obtained from the comparison example described above and the mixture is heated to 40° C. 18.7 g (0.168 mol) of dimethyl sulfate are added via a dropping funnel over a period of 2 hours and the pH is kept at 7 by addition of 6.4 g of a 10% strength by weight aqueous sodium hydroxide solution.

Thereafter, the 3-hydroxy-2,4,5-trifluorobenzoic acid can no longer be detected. However, 15.6 g (70.9 mmol) of methyl 3-methoxy-2,4,5-trifluorobenzoate, corresponding to a yield of not less than 87% of theory, have formed.

The somewhat lower yield compared with Example 2b) is to be attributed to the pretreatment of the reaction mixture.

EXAMPLE 3 a) Preparation of 2,3,4,5-tetrafluorobenzoic acid by decarboxylation of tetrafluorophthalic acid The reaction proceeds in accordance with the following equation:

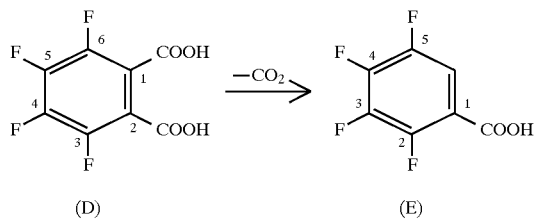

2206 g of a water-containing mixture (water content 8.3% by weight), which comprises 311 g (1.31 mol) of tetrafluorophthalic acid (D) in a mixture of 150 g of trialkylamines having 8 to 10 carbon atoms per alkyl radical (Hostarex A327), 100 g of diphenylmethane and 300 g of xylene, are initially introduced into a glass flask, while stirring.

The pH is brought to 6 to 7 with 96% strength sulfuric acid and the mixture is heated at 110° C. under vigorous reflux for 9 hours. The mixture is then heated at 110° C. with thorough stirring and 97.8 g of water and 179.1 g of xylene are distilled off in the course of 2 hours. The reaction mixture which remains after the removal by distillation comprises 234.9 g (1.21 mol, corresponding to 92.4% of theory) of 2,3,4,5-tetrafluorobenzoic acid (E), determined by means of calibrated HPLC analysis.

b) Preparation of ethyl 2,3,4,5-tetrafluorobenzoate

The reaction proceeds in accordance with the following equation

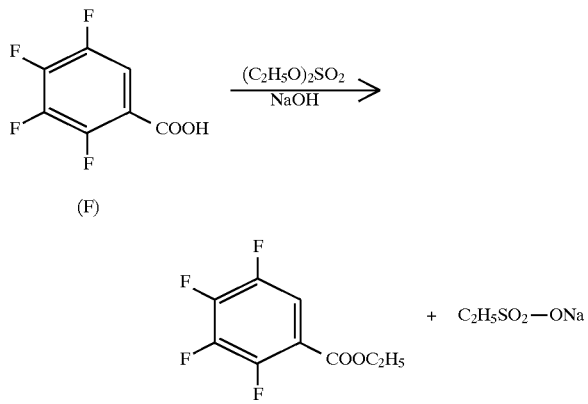

The distillate separated off in Example 3a) (97.8 g of water and 179.1 g of xylene) is added to the reaction mixture obtained from Example 3a). 856.9 g (5.55 mol) of diethyl sulfate are then added dropwise at a temperature of 40° C. over a period of 4 hours, while stirring, and the pH is kept in a range from 7 to 8 by addition of aqueous sodium hydroxide solution. The mixture is subsequently stirred for 75 minutes, 10 g of ammonium chloride are added and the mixture is subsequently stirred for 2 hours. It is filtered at pH 8.2 and the aqueous phase is separated from the organic phase, with the addition of 600 g of xylene and 1000 g of diphenylmethane. 1031.7 g of distillate which, determined by means of calibrated gas chromatography analysis, comprises 245 g (1.1 mol) of ethyl 2,3,4,5-tetrafluorobenzoate, corresponding to a yield of 84% over 2 stages, based on the tetrafluorophthalic acid employed, are obtained from the organic phase (2330 g) by distillation at a temperature up to 193° C. under a reduced pressure to 4 to 5 mbar (2 to 3 mm Hg).

If 200 g of quinoline are used instead of the trialkylamine mixture (Hostarex A327), the batch proceeds completely analogously. 234.5 g (1.07 mol, corresponding to 81.3% of theory) of ethyl 2,3,4,5-tetrafluorobenzoate, determined by means of calibrated HPLC analysis, are obtained. If 300 g of collidine are used, the yield of ethyl 2,3,4,5-tetrafluorobenzoate is 82.1% of theory.

EXAMPLE 4

Preparation of methyl 3-methoxy-2,4,5-trifluorobenzoate (addition of a phase transfer catalyst to assist the thorough mixing)

The reaction follows the equation mentioned in Example 2b, by esterification of 3-hydroxy-2,4,5-trifluorobenzoic acid (B).

10% strength by weight aqueous sodium hydroxide solution is added, while stirring, to 1 kg of an aqueous solution prepared analogously to Example 2a, which has been separated off from the water-insoluble amines, until a pH of 7.5 is established. The mixture comprises 54.6 g (0.284 mol) of 3-hydroxy-2,4,5-trifluorobenzoic acid (B), determined by HPLC analysis (calibration with an external standard). 20 g of Hostarex A327 (see also Example 2b) and 20 g of a 50% aqueous solution of a dimethylbenzylcoconut alkyl ($C_{10}$–$C_{18}$)ammonium chloride having an average molecular weight of 382.5 (Dodigen 226) are added, while stirring by means of a magnetic stirrer. The mixture is then heated to 50° to 52° C., 329.2 g (2.61 mol) of dimethyl sulfate are added dropwise in the course of 4.5 hours and the pH of the stirred mixture is kept at 7 to 7.5 by addition of 10% strength by weight aqueous sodium hydroxide solution (consumption 133 g). The pH of the mixture comprising the water, the mixture of water-insoluble trialkylamines having 6 to 8 carbon atoms per alkyl radical (Hostarex A 327) and the 3-hydroxy-2,4,5-fluorobenzoic acid is checked by means of a calibrated pH electrode immersed in the aqueous phase.

The reaction has ended after a subsequent stirring time of 2 hours at pH 7 to 7.5 and 50° to 52° C. (determined by HPLC analysis). 50 g of xylene are added and the organic phase is separated off. This step is repeated twice.

The combined organic phases comprise (determined by calibrated HPLC analysis) 55.5 g (0.252 mol) of methyl 3-methoxy-2,4,5-trifluorobenzoate, corresponding to a yield of 88.7%, based on the 3-hydroxy-2,4,5-trifluorobenzoic acid (B) employed.

We claim:

1. A process for the preparation of a compound of the formula (1)

$$R^1R^2R^3R^4R^5ArCOOR \qquad (1)$$

in which $R^1$, $R^2$, $R^3$, $R^4$ and $R^5$ are identical or different and are hydrogen, a halogen, an alkyl or alkoxy group having 1 to 6 carbon atoms or OR, NHR, $NR_2$, SR or COOR, in which R is an alkyl radical having 1 to 4 carbon atoms, Ar is an aryl radical having 6 to 12 carbon atoms and the radical R shown in formula (1) has the above meaning, which comprises reacting a compound of the formula (2)

$$R^1R^2R^3R^4R^5ArCOOH \qquad (2)$$

in which $R^1$, $R^2$, $R^3$, $R^4$ and $R^5$ are identical or different and are hydrogen, a halogen, an alkyl or alkoxy group having 1 to 6 carbon atoms, OH, $NH_2$, NHR, SH or COOH and Ar has the same meaning as in formula (1), with a sulfate of the formula $(RO)_2SO_2$, in which R has the above meaning, in the presence of a water-insoluble tertiary amine and water at a temperature of 10° to 120° C. in the presence or absence of a water-insoluble solvent and with the addition of a base, at a pH of 5 to 12.

2. The process as claimed in claim 1, wherein $R^1$ and $R^2$ of the formula (2), are identical or different and are hydrogen, an alkyl group having 1 to 6 carbon atoms, OH, NH2 or COOH.

3. The process as claimed in claim 1, wherein $R^1$ and $R^2$ of the formula (2) are identical or different and are hydrogen, OH or COOH.

4. The process as claimed in claim 1, wherein $R^1$ or $R^2$ of the formula (2) is OH or COOH.

5. The process as claimed in claim 1, wherein $R^1$ or $R^2$ of the formula (2) is OH.

6. The process as claimed in claim 1, wherein $R^3$, $R^4$ and $R^5$ of the formula (2) are identical or different and are hydrogen, a halogen or an alkyl or an alkoxy group having 1 to 6 carbon atoms.

7. The process as claimed in claim 1, wherein $R^3$, $R^4$ and $R^5$ of the formula (2) are identical or different and are hydrogen, fluorine, chlorine or an alkyl group having 1 to 6 carbon atoms.

8. The process as claimed in claim 1, wherein $R^3$, $R^4$ and $R^5$ of the formula (2) are identical or different and are hydrogen or flourine.

9. The process as claimed in claim 1, wherein Ar of the formula (2), is a phenyl radical, biphenyl radical or naphthyl radical.

10. The process as claimed in claim 1, wherein Ar of the formula (2), is a phenyl radical.

11. The process as s claimed in claim 1, wherein the sulfate of the formula $(RO)_2SO_2$ is dimethyl sulfate, diethyl sulfate or dibutyl sulfate.

12. The process as claimed in claim 1, wherein the sulfate of the formula $(RO)_2SO_2$ is dimethyl sulfate or diethyl sulfate.

13. The process as claimed in claim 1, wherein the sulfate of the formula $(RO)_2SO_2$ is employed in a ratio, based on each group R to be introduced into the compound of the formula (2), of (1 to 10): 1.

14. The process as claimed in claim 1, wherein said water insoluble tertiary amine is a trialkylamine having 4 to 20 carbon atoms per alkyl radical, a mixture of these trialkylamines, an N-containing heterocyclic compound or a mixture of the above amines.

15. The process as claimed in claim 14, wherein said water insoluble tertiary amine is a trialkylamine having 6 to 14 carbon atoms per alkyl radical or a mixture of these trialkylamines.

16. The process as claimed in claim 1, wherein said water insoluble tertiary amine is a mixture of trialkylamines having 6 to 12 carbon atoms per alkyl radical, which contain identical or different straight-chain or branched alkyl radicals.

17. The process as claimed in claim 1, wherein the water-insoluble tertiary amine and the compound of the formula (2) are employed in a molar ratio of(0.01 to 10):1.

18. The process as claimed in claim 1, wherein the reaction is carried out at 20° to 80° C.

19. The process as claimed in claim 1, wherein the reaction is carried out at 30° to 60° C.

20. The process as claimed in claim 1, wherein said water insoluble solvent is an aliphatic hydrocarbon, a halogenated aliphatic hydrocarbon, an aromatic hydrocarbon, a halogenated aromatic hydrocarbon, an aromatic ether or a mixture of these solvents.

21. The process as claimed in claim 1, wherein said base is an aqueous solution of an alkali metal hydroxide or alkaline earth metal hydroxide.

22. The process as claimed in claim 1, wherein the reaction is carried out at a pH of 6 to 10.

23. The process as claimed in claim 1, wherein the reaction is carried out at a pH of 7 to 8.5.

24. The process as claimed in claim 1, wherein the reaction is carried out in the presence of a phase transfer catalyst.

25. The process as claimed in claim 24, wherein said phase transfer catalyst is a tetra($C_1$–$C_{20}$)alkylammonium salt, tri($C_1$–$C_{20}$) alkylbenzylammonium salt or di($C_1$–$C_{20}$) alkyldibenzylammonium salt, the benzyl radical of which is unsubstituted or substituted by Cl, Br, ($C_1$–$C_4$)alkyl or ($C$,-$C_4$)alkoxy.

26. The process as claimed in claim 24, wherein said phase transfer catalyst is a quaternary ammonium halide which contains one or more coconut-($C_{10}$–$C_{18}$) alkyl radicals.

27. The process as claimed in claim 24, wherein said phase transfer catalyst is a dicoconut ($C_{10}$–$C_{18}$) alkyldimethylammonium halide or dimethylbenzlcoconut ($C_{10}$–$C_{18}$)alkylammonium halide.

28. The process as claimed in claim 24, wherein the phase transfer catalyst is employed in an amount of 0.05 to 10% by weight, based on the aqueous phase.

29. The process as claimed in claim 13, wherein the sulfate of the formula $(RO)_2SO_2$ is employed in a ratio, based on each group R to be introduced into the compound of formula (2), of (1.1 to 5):1 and the water-insoluble tertiary amine and the compound of the formula (2) are employed in a molar ratio of (0.05 to 3):1.

30. The process as claimed in claim 13, wherein the sulfate of the formula $(RO)_2SO_2$ is employed in a ratio, based on each group R to be introduced into the compound of formula (2), of (1.2 to 1.5):1 and the water-insoluble tertiary amine and the compound of the formula (2) are employed in a molar ratio of (0.05 to 1):1.

31. The process as claimed in claim 24 wherein said phase transfer catalyst is a quaternary ammonium salt of the formula

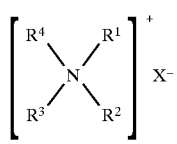

in which $R^1$, $R^2$, $R^3$ and $R^4$ are identical or different and are hydrocarbon radicals having a total of 10 to 50 carbon atoms and $X^-$ is a halide ion, hydrogen sulfate ion or hydroxyl ion.

* * * * *

UNITED STATES PATENT AND TRADEMARK OFFICE
CERTIFICATE OF CORRECTION

PATENT NO.   : 5,874,608
DATED        : February 23, 1999
INVENTOR(S)  : Ralf Pfirmann and Theodor Papenfuhs It is certified that error appears in the above-indentified patent and that said Letters Patent is hereby corrected as shown below:

In the Claims:

Column 13, line 17, delete "NH2" and substitute therefor --$NH_2$--.

Signed and Sealed this

Sixth Day of July, 1999

Attest:

Q. TODD DICKINSON

*Attesting Officer*  *Acting Commissioner of Patents and Trademarks*